United States Patent [19]

Chang et al.

[11] Patent Number: 5,419,766
[45] Date of Patent: May 30, 1995

[54] CATHETER WITH STICK PROTECTION

[75] Inventors: Joseph J. Chang, Avon; Dennis M. Bialecki, Oxford; Mark A. Panzera, Bristol, all of Conn.; Gerald J. Kovalic, Odessa, Fla.

[73] Assignee: Critikon, Inc., Tampa, Fla.

[21] Appl. No.: 127,536

[22] Filed: Sep. 28, 1993

[51] Int. Cl.6 ............................................. A61M 5/00
[52] U.S. Cl. ................................. 604/110; 604/163; 604/198
[58] Field of Search ........ 604/192, 198, 110, 162-165, 604/171, 263

[56] References Cited

U.S. PATENT DOCUMENTS

| | | | |
|---|---|---|---|
| 4,725,267 | 2/1988 | Vaillancourt | 604/192 |
| 4,747,831 | 5/1988 | Kulli . | |
| 4,762,516 | 8/1988 | Luther et al. . | |
| 4,778,453 | 10/1988 | Lopez | 604/110 |
| 4,790,828 | 12/1988 | Dombrowski et al. . | |
| 4,804,371 | 2/1989 | Vaillancourt . | |
| 4,826,490 | 5/1989 | Byrne et al. . | |
| 4,832,696 | 5/1989 | Luther et al. . | |
| 4,834,718 | 5/1989 | McDonald | 604/163 |
| 4,846,805 | 7/1989 | Sitar | 604/165 |
| 4,850,961 | 7/1989 | Wanderer et al. . | |
| 4,892,521 | 1/1990 | Laico et al. | 604/192 |
| 4,917,669 | 4/1990 | Bonaldo . | |
| 4,931,048 | 6/1990 | Lopez . | |
| 4,950,252 | 8/1990 | Luter et al. . | |
| 4,952,207 | 8/1990 | Lemieux . | |
| 4,964,854 | 10/1990 | Luther . | |
| 4,978,344 | 12/1990 | Dombrowski et al. . | |
| 4,990,141 | 2/1991 | Byrne et al. . | |
| 4,994,041 | 2/1991 | Dombrowski et al. . | |
| 5,000,740 | 3/1991 | Ducharme et al. . | |
| 5,013,304 | 5/1991 | Russell et al. . | |
| 5,019,049 | 5/1991 | Haining . | |
| 5,053,014 | 10/1991 | Van Heugten . | |
| 5,084,030 | 1/1992 | Byrne et al. . | |
| 5,085,648 | 2/1992 | Purdy et al. . | |
| 5,205,829 | 4/1993 | Lituchy . | |
| 5,215,528 | 6/1993 | Purdy et al. . | |

Primary Examiner—John D. Yasko
Attorney, Agent, or Firm—Joseph F. Shirtz

[57] ABSTRACT

A new catheter stick protector is described having a metal flap clip which snaps down into place to prevent return of the needle through the protector device once withdrawn. The device is small and received over the needle to provide an interface between the needle hub and the hub of a catheter like product. A sleeve of hydrophobic or fluid impermeable material is provided and attached at one end to the needle hub and at a second end to the tip protector. The length of the material is selected to hold the tip protector in a position just extending beyond the tip of the needle of a catheter inserter.

22 Claims, 11 Drawing Sheets

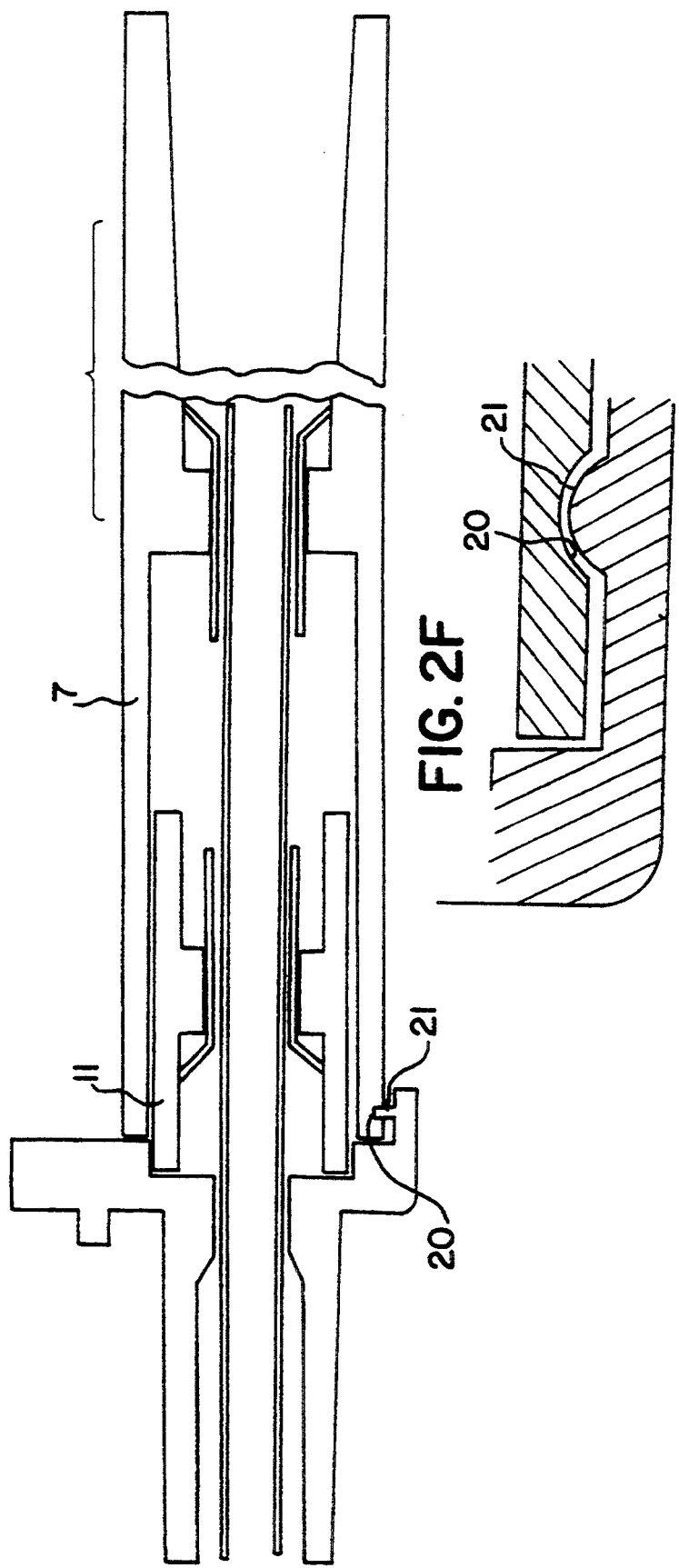

CATHETER WITH STICK PROTECTION

FIELD OF THE INVENTION

The invention relates to the field of medical devices and in particular medical apparatus for puncturing the skin layer of a patient to embrace a tubular catheter.

BACKGROUND OF THE INVENTION

Essentially catheters and in particular intravenous catheters are of two overall types. The first type is a through the needle catheter in which the tubular catheter product is emplaced in a vein by being carried within a tubular needle. Once implanted the needle is withdrawn and either split to remove it from the catheter or left in a contained condition on the catheter. Through the needle catheters, however, are in limited use due to their difficulty of use and the difficulty of removing the needle. Further the needle being larger than the catheter creates a larger opening upon insertion than the outer diameter of the catheter. This permits blood leakage around the outer area of the catheter unless a swelling catheter is used.

The second and more prevalent type of catheter is the over-the-needle catheter in which a tubular catheter is placed over an inserting sharpened cannula or needle. The needle is used to pierce the skin and enter the vein of the patient and the catheter is thereafter threaded off the needle and the needle removed. This permits coupling of the catheter to medical equipment.

In an over-the-needle catheter situation, the health care worker is exposed to the sharpened tip of the cannula and to the surface of the cannula which may be contaminated with bodily fluids. Therefore, many efforts have been made to protect the health care worker from exposure to the risk of this occurrence.

U.S. Pat. No. 4,725,267 to Vaillancourt relates particularly to a post injection needle sheath and not to a catheter. The needle sheath encloses the sharpened end of a needle which is used with a syringe. The sheath is initially in a compact and secured condition on the needle hub and has a substantial portion of the needle exposed for insertion into a patient or vial. After use the sheath is extended over the needle and a cap caps the needle in order to prevent puncture of the health care worker.

U.S. Pat. No. 4,747,831 chose an automatic catheter device in which the inserting cannula is withdrawn into a housing through the operation of a spring.

U.S. Pat. No. 4,762,516 describes an assembly of a needle catheter protector. This assembly comprises an elongated housing which mounts to the needle. A needle guard is slidably mounted within the housing and is adapted to be moved forward along the needle. Following use, the needle and housing are retracted and the needle guard permanently locks with the housing while it covers the needle.

Other patents relating to stick protection devices are U.S. Pat. Nos. 4,778,453; 4,790,828; 4,804,371, which all relate to catheter type devices. U.S. Pat. No. 4,826,490 relates particularly to a syringe type product and a movable housing for enclosing the used needle of a syringe.

U.S. Pat. No. 4,832,696 relates to an assembly of a needle and a protector for the needle. The assembly comprises an elongated housing which mounts to the needle. A needle guard is slidably mounted within the housing and is adapted to be moved forward along the needle. Following use the needle and housing are retracted and the needle guard becomes permanently locked with the housing as it covers the needle. This patent is of the same family of the '516 patent described above.

Further patents directed to needle stick protection include U.S. Pat. No. 4,834,718 entitled Safety Needle Apparatus. This patent describes an intravenous catheter apparatus which protects a clinician from accidental puncture which may result in the transfer of dangerous infections. The catheter is introduced with the aid of a needle which is thereafter withdrawn from the patient's body into a protective housing without exposing the needle during intermediate stages of the process. In particular, means are provided for latching the housing in place after the needle is withdrawn and for locking a catheter hub in place until the needle is withdrawn. Withdrawal and locking are affected in one continuous motion.

U.S. Pat. No. 5,215,528 is entitled Catheter Introducer Assembly Including Needle Tip Shield. This patent describes an assembly where a needle is modified to have an enlarged diameter near the tip. A needle tip cover is slidably mounted on the needle such that it is slid to a point wherein it engages the enlarged portion of the shaft to prevent removal of the tip therefrom. The catheter is releasably mounted over the tip cover. It is stated in this patent that the enlarged portion also serves to provide a leak proof seal between the catheter and the needle. However, it has been found in practice that a device substantially conforming to the '528 patent has significant problems. Initially if the widened portion of the needle is large enough to create the "leak proof seal" the friction on removal of the catheter may be so great as to create a commercially unacceptable apparatus. The friction upon removal of the catheter from the needle must be low enough to permit ease of removal of the needle. In order to provide this low friction the expansion of the needle cannot engage the inner portion of the tubular catheter tightly enough to provide the "leak proof seal". Therefore, catheters of this design leak a significant amount around the needle and in the space between the needle and catheter. Such a structure and device are self defeating in that the exposure to the blood is increased through the leakage rather than decreased through the use of a cover and tip protection device.

SUMMARY OF THE INVENTION

Therefore it has been found that a catheter can be devised having a small introducer body permitting ease of use while still maintaining a separation between the needle and the health care worker upon removal from the catheter after introduction. In the invention a catheter introducer assembly is provided which comprises a needle having a tip at a distal end thereof. A hub is attached at a proximal end of the needle and a tip protector is provided which is slidable along the length of the needle. The tip protector may comprise means for attaching the tip protector to the hub to limit movement of the tip protector beyond the tip. This means for attaching the tip protector may take the form a mesh material having a hydrophobic coating or of a substantially continuous film of polyester or the like. Holding means is provided for preventing movement of the tip protector toward the hub once the tip protector has been moved to its position covering the tip. Thus the needle is encased completely within the tip protector and its holding means.

Additionally, a latex gasket may be formed in the tip protector to reduce the back flow of fluid along the outer surface of the needle. The latex gasket is soft and pliable and therefore does not provide a greatly increased friction in the removal of the needle. Rather than the latex gasket a valve may be formed in the protector to reduce the back flow of fluid from the catheter into the tip protector once the needle is removed. This valve may comprise a flap which is movable between a first position adjacent to an outer surface of the needle and a second position where the flap occludes communication between the catheter hub and the inner space of the tip protector. For example, the flap may rotate from the first position to the second position or may slide in a direction transverse to the longitudinal access of the needle from the first position to the second position. In the rotating mode of the invention the flap may be created using a living hinge of sufficient resilient memory to move the flap from said first position to the second position. In the transverse moving type of valve a spring or magnet may be provided in order to bias the valve element across the path of the needle once the needle is removed.

In order to improve operation of the protection device a detent means may be formed on a first of either the catheter hub or the needle protector and a bump on the other may be formed such that cooperation between the bump and detent hold the tip protector and hub in connected condition until the needle is fully retracted within the tip protector. At this time the additional pulling force of the person applying the apparatus would overcome the interengagement of the bump and detent and withdraw the tip protector from the hub.

The tip protector may operate through the use of a cylindrical clip which is inserted into the tip protector. The needle would ride within the inner space of the clip and a flap is formed in the outer surface of the clip to provide the locking mechanism for locking the tip protector in place. By plastically deforming a flap formed of the cylindrical clip radially inward into the space defined by the clip, a locking mechanism may be formed. This flap may then be moved in a resilient fashion to the outer surface of the needle upon insertion of the needle. Once the needle is withdrawn beyond the flap, the resilient nature of the plastic deformation previously performed would bias the flap into an interfering position in front of the needle preventing the reinsertion of the needle through the tip protector.

The flap may be formed such that it is either curved or substantially planar.

BRIEF DESCRIPTION OF THE DRAWINGS

The invention will now be described with reference to the accompanying drawings wherein:

FIG. 2E is a partial cross-sectional view of the catheter hub and tip protector means of the invention;

FIG. 2F is a partial cross-sectional view of the interengagement of the catheter hub and tip protector means of the invention;

DESCRIPTION OF THE PREFERRED EMBODIMENT

Figure 1:
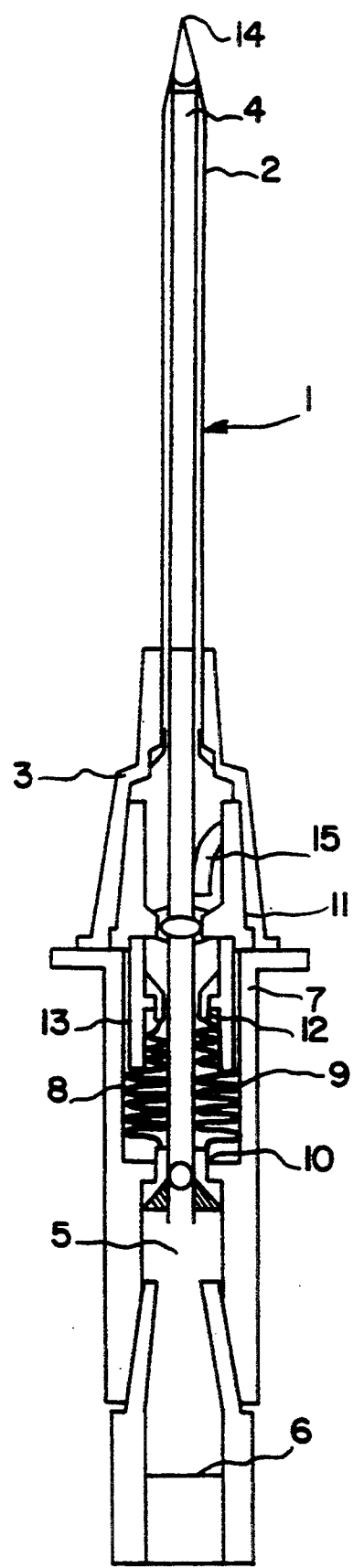
FIG. 1 is a cross-sectional view of a catheter assembly formed according to the invention.

FIG. 1 displays the present invention overall in a catheter device. The catheter is of the type described as an over-the-needle catheter. In an over-the-needle catheter the catheter 1 is made up of a catheter tube 2 and catheter hub 3. The catheter hub 3 may be of any conventional formation such as that with a tapered internal luer lock for receipt of a male lure in a standard medical apparatus.

The catheter is fitted over a sharpened needle or cannula 4 which is hollow to permit flash back during insertion of the needle and catheter assembly into a vein of a patient. The needle communicates with a flash chamber 5 which is partially sealed by a flash plug 6 which permits the passage of air to permit the back flow or flash back of blood into the chamber to indicate appropriate puncture of the vein. The flash chamber is part of a needle hub 7 to which the needle or cannula 4 is mounted in a conventional manner.

The needle hub 7 is formed with a sleeve chamber 8 partially defined by the needle hub. The sleeve chamber 8 receives therein a corrugated sleeve 9 the function and form of which will be described below. The corrugated sleeve 9 is attached at its proximal end 10 to the needle hub. A tip protector 11 is formed and attached to the distal end 12 of the corrugated sleeve 9.

It should be understood that by using the term corrugated sleeve it is intended that the description not be limited simply to corrugated materials. The sleeve may be woven such that it may be shortened and increased in diameter or may merely be gathered in the sleeve chamber 8 instead of corrugated.

The tip protector 11 has at its distal end a substantially male lure fitting formation to be received within the catheter hub 3. At its proximal end the tip protector is received partially within the sleeve chamber 8 to further define the sleeve chamber for containment of the corrugated sleeve 9. In the preferred embodiment a tip protector base 13 is received within the sleeve chamber 8. The tip protector base 13 is at the proximal end of the tip protector and provides the attachment means for the corrugated sleeve 9.

The sleeve 9 is attached at its ends by inserting an eyelet into the tube. The eyelet in turn is mounted to the tip protector and needle hub. This mounting may be by interference fit, ultrasonic welding, adhesives or the like.

The tip protector 11 is designed to be slidably received on the needle 4 such that it may slide from a proximal location where the tip protector base is substantially received within the sleeve chamber 8 to a position which is extended therefrom in which the tip protector covers the distal end 14 of the needle 4. The extended form of the device is more easily seen in FIG. 2C. Referring to that Figure it is noted that the catheter has been emplaced in the patient and the tip protector is received over the end of the needle. A clip 15 has moved into position protecting the tip of the needle and a formed gasket 16 of the type described in U.S. Pat. No. 5,092,845 is provided in the protector means in order to prevent the flow of blood back around the needle and along the needle shaft. Although this gasket may or may not be present any blood which does leak beyond the gasket area of the tip protector to the needle is sufficiently isolated from user contact through the sleeve which extends between the tip protector 11 and the needle hub 7. The sleeve isolates any body fluids which may be on the needle from the user by providing a substantial moisture impervious isolator about the needle.

Figure 2A:
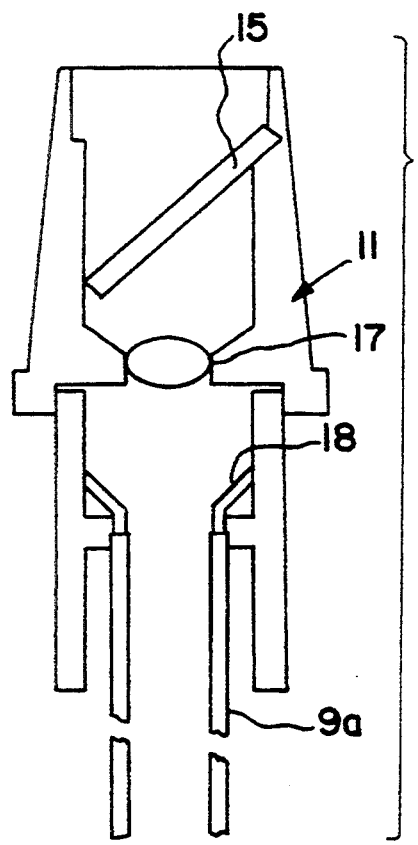
FIG. 2A is a cross-section through the tip protector portion of the introducer.
Figure 2B:
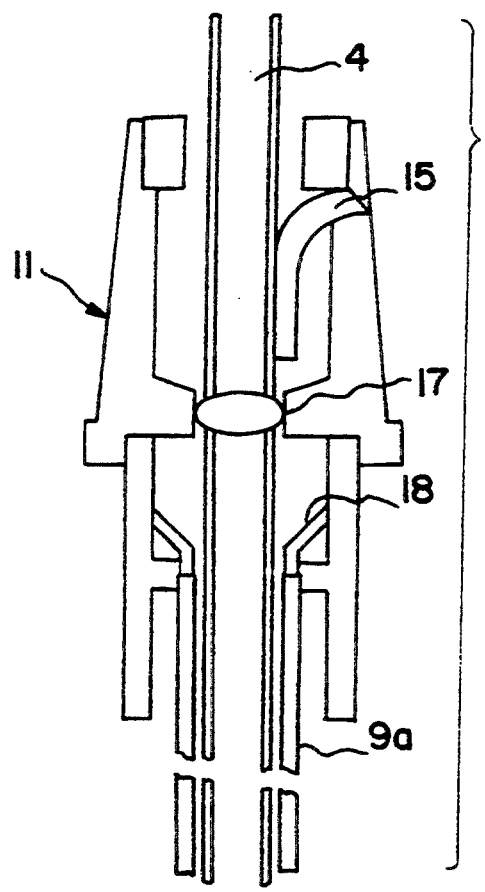
FIG. 2B is a cross-section of the tip protector of FIG. 2A having a needle inserted therein.
Figure 2C:
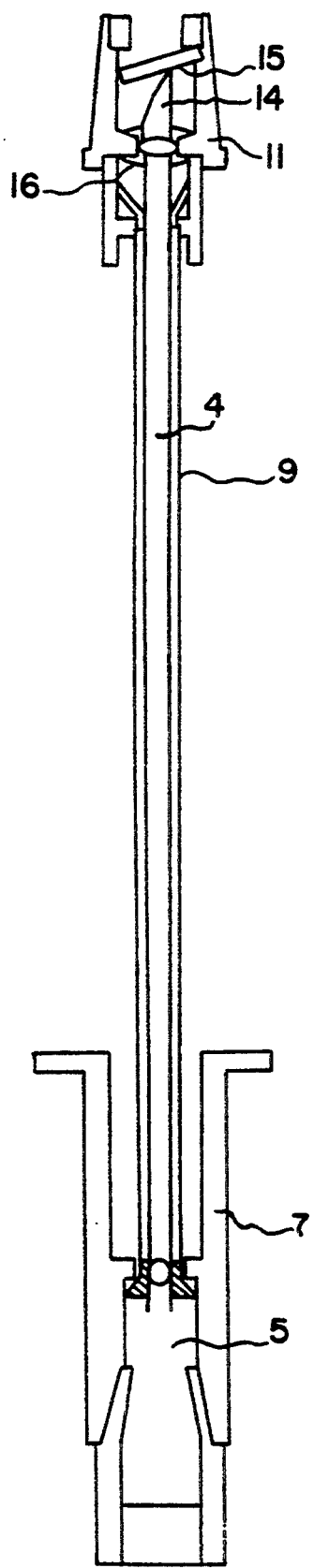
FIG. 2C is a cross-sectional view of an inserter assembly after withdrawal of the needle.

FIGS. 2A and 2B show the construction of the tip protector. FIG. 2A shows the tip protector 11 Raving a clip 15 in its relaxed or fired state. That is, the position of clip 15 is the position the clip would obtain after the needle is withdrawn beyond the clip or, depending on the fabrication steps, prior to insertion of the needle into the clip in the assembly method. The clip 15 is resiliently mounted within the tip protector 11 such that the presence of the needle passing through a passage formed in the tip protector holds the clip 15 in a stressed position as shown in FIG. 2B. The tip protector has a narrowed portion 17 which operates to provide a substantial basis for a gasket which will be described below and further for stabilizing the needle within the tip protector. The sleeve 9a in its extended position is shown in both FIGS. 2A and 2B. The sleeve 9a is mounted within an opening defined in the base of the tip protector through the use of an eyelet 18 which operates to mount and mechanically hold the sleeve within the base. In the fabrication of the tip protector it may be seen that the tip base 13 may be constructed to receive the sleeve 9 in a substantially corrugated or uncorrugated fashion. An eyelet 18 is passed into the sleeve and through use of adhesive or mechanical means such as ultrasonic welding the eyelet sleeve and tip protector base are fixed to one another. After this is done the tip protector itself may be fabricated by attaching the tip protector 11 to the tip protector base 13. Again, the tip protector 11 may be attached to the tip protector base either by adhesives, mechanical means or ultrasonic welding, for example.

Figure 2D:
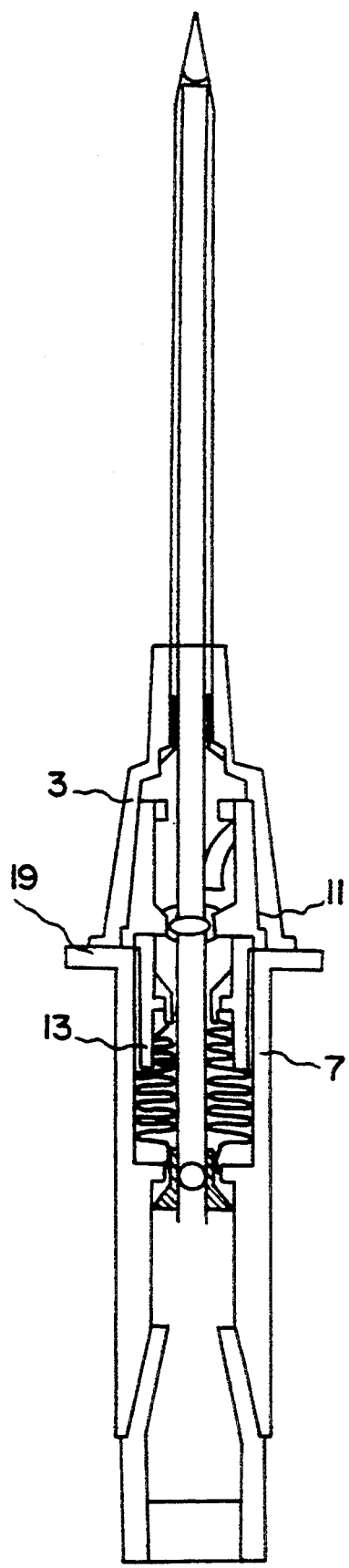
FIG. 2D is a cross-sectional view of a catheter inserter assembly and catheter according to the invention.

Referring now to FIG. 2D certain of the features of the present invention are shown. The needle hub 7 is formed with an abutment surface 19 which receives thereon the proximal end of the tip protector 11 when the tip protector base 13 is received within the sleeve chamber 8. As is seen in FIG. 2D the tip protector base slides into the sleeve chamber and the proximal end of the tip protector abuts abutment surface 19 in order to prevent further inward motion of the tip protector and provide a solid assembly for insertion into a patient's vein. Further the catheter assembly which is mounted over the needle and on the tip protector in surrounding relation also abuts against abutment surface 19. This prevents the tip protector 11 from being forced too far into the hub 3 of the catheter i to excessively increase the removal force of the catheter. As is shown in the blown up portion of FIG. 2D the tip protector may be formed such that a hermetic seal is created only at the forward portion of the nose piece in a small area contact seal.

It may be found in certain constructions that the sleeve material may have sufficient memory to urge the tip protector away from the needle hub. That is the memory of the sleeve material creates a spring force in the sleeve material forcing the tip protector away from the hub and out over the end of the needle. In order to prevent this a holding mechanism may be provided between the tip protector and the needle hub. This device is shown in FIG. 2E. A detent 20 is formed in an outer edge of the needle hub along the outer surface adjacent the distal end. A bump or knob 21 is formed on the proximal portion of the tip protector and is received in the normal assembled position within the detent 19. In this way the knob 21 and detent 20 act to hold the tip protector and needle hub in their relative positions. The knob and detent also provide a position directional indication during assembly in order to align the needle hub and tip protector. This alignment facilitates the operation of the clip 15 such that as it slides along the cannula 4 it is positioned along the longest side of the needle. Once it clears the tip of the needle the flap portion of clip 15 can freely swing down into contact with an opposing surface making an audible sound or click.

Figure 3A:
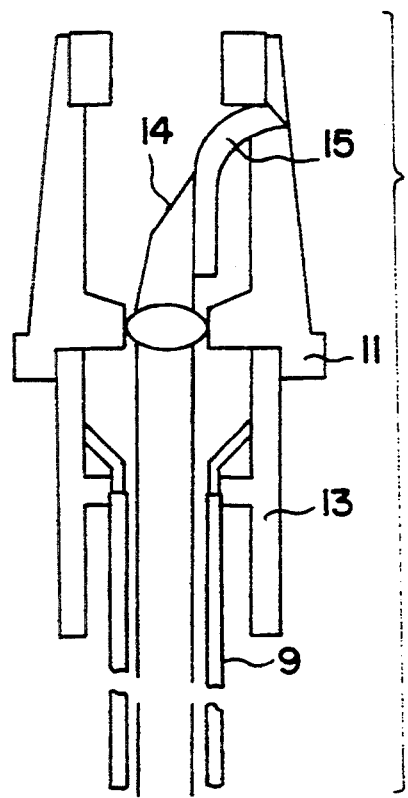
FIGS. 3A and 3B are cross-sectional views of a tip protector of the invention showing the operation of a flap or locking device.
Figure 3B:
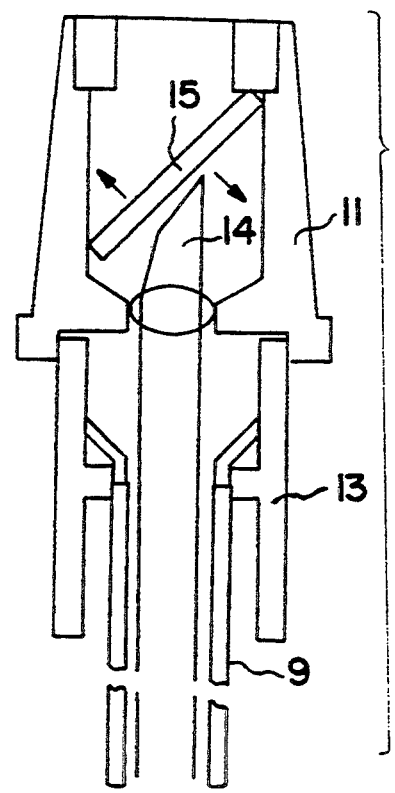

The operation of the clip 15 is shown with reference to FIGS. 3A and 3B. As the tip protector 11 is slid along the length of the needle 4 it reaches a point adjacent the end of the needle where the clip is still in its stressed position at one side of the clip protector. Preferably the clip rides along the longest side of the cannula, that is the side of the cannula leading to the extreme distal point. Once clearing the distal point as shown in FIG. 3B the clip under the inherent resilient spring force snaps from its position adjacent the needle to a position against the opposite side wall of the tip protector 11. This motion from the stress position to the contact with the opposing wall creates an audible click which provides the user with a sensation indicating that the protector is in its appropriate position.

Figures 1, 3C:
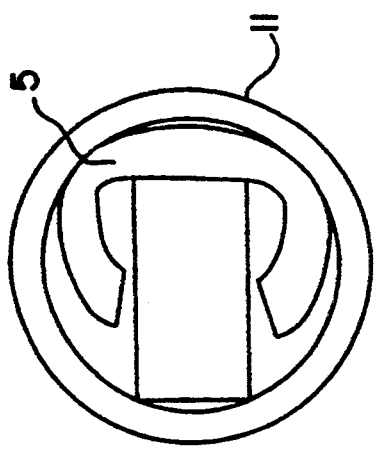
FIG. 3C shows the emplacement of a locking clip within the tip protector.
Figures 3, 3C:
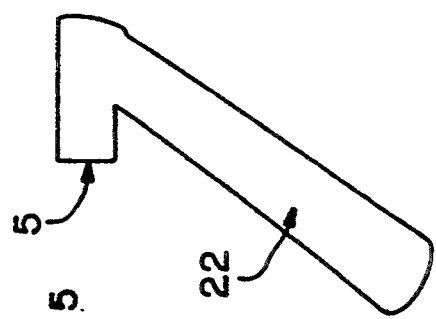
Figures 2, 3C:
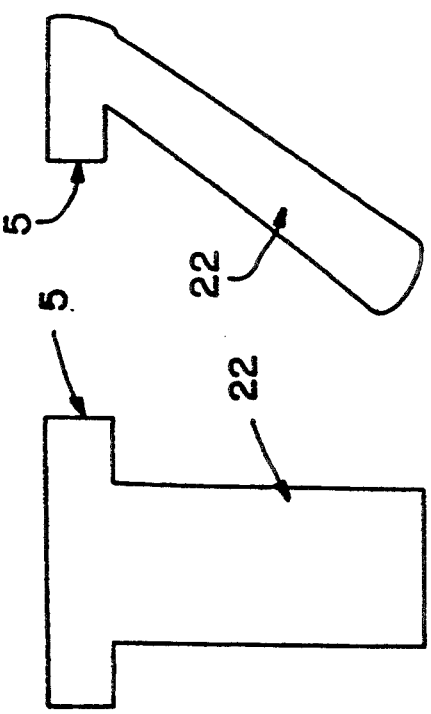
Figure 4A:
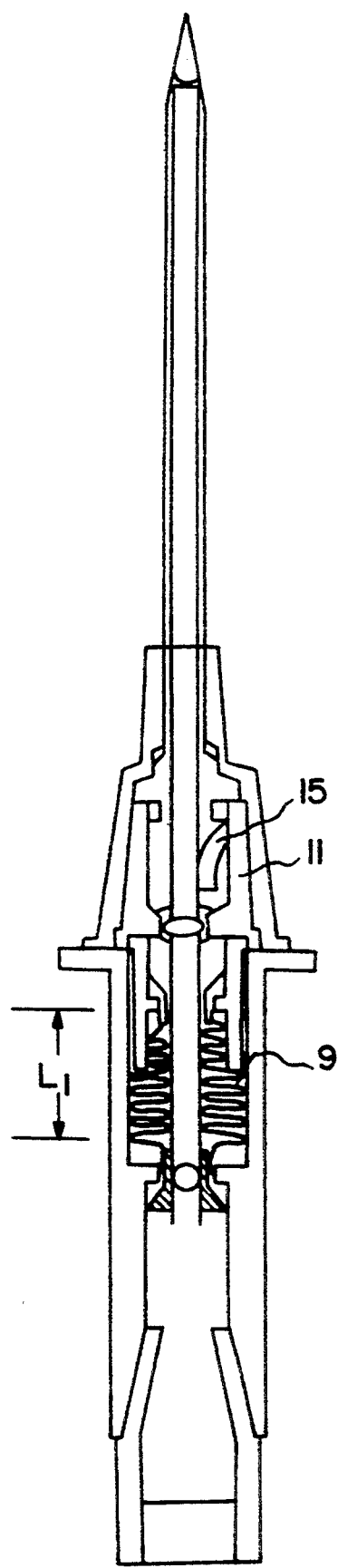
FIGS. 4A and 4B are views of an alternate embodiment of the locking clip.
Figure 4B:
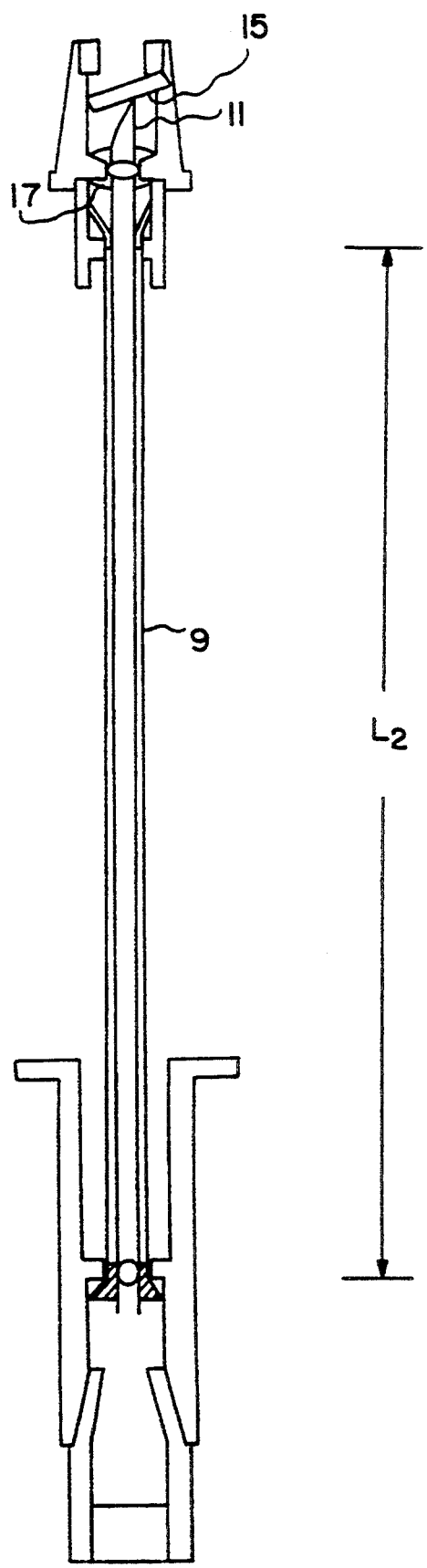

Formation of the clip itself is shown with respect to FIG. 3C. A T-shape piece of metal is formed having the arms of the T bent around in order to provide a base of support for the clip. The lower portion or body of the T is used to form the actual clip itself. Once bent into a circular position the arms may be received within the internal space of the tip protector in a interfering relationship. The body 22 of the clip is bent downward beyond the elastic limit of the metal and subsequently heat treated to create a resilient property in order that the body, if biased or stressed, always desires to return to this flexed position.

Figures 1, 5A:
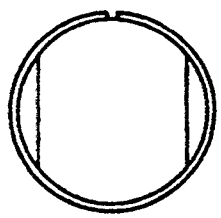
FIGS. 5A and 5B show two embodiments of antistick clip made of a cylindrical tube stock.
Figures 2, 5A:
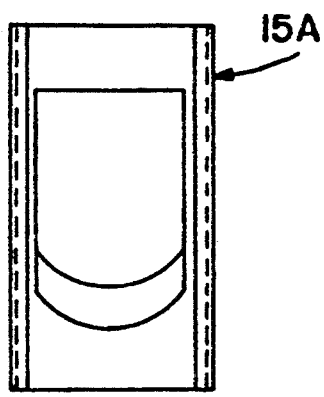
Figures 3, 5A:

There are several different forms that the clip may take. For example, the anti-stick clip 15A (FIG. 5A) may be made of a cylindrical piece of metal such as tube stock which has a tab punched therein and bent toward the inside of the cylinder. The tab is formed inward such that the tab is plastically worked to the point that the tab contacts the opposing inside wall of the tube. The tab may be formed intermediate the cylinder body or may extend all of the way to the end of the cylinder. The tab may be cut from the cylinder where the bottom tab edge is also the end edge of the cylinder prior to formation of the tab. Alternatively, the tab may also be formed with an arcuate end wall or edge such that the edge defines a substantially similar shape to the internal surface of the clip itself. In this way rather than their being corner contact of the tab against the opposing inner wall there is substantially linear contact increasing the chances of the audible click being created.

Figures 1, 5B:
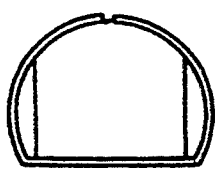
Figures 2, 5B:
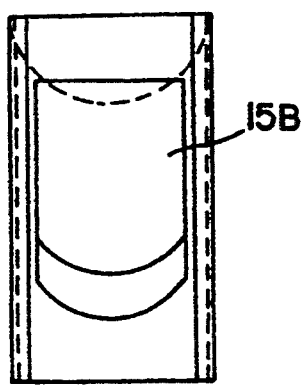
Figures 3, 5B:
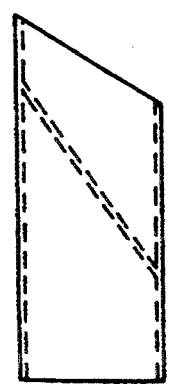

A modified clip is also been formed and is described with reference to FIG. 5B. In this type of clip 15B rather than a cylindrical shape a substantially "D" shaped cross-section is provided. The tab is cut or formed from the flattened side of the D. This provides several advantages and is preferred in the present invention.

First, by forming the tab out of a flattened surface a more consistent plastic deformation may be provided and a linear hinge is formed which increases the reliability of the clip. Second, once received within a cylindrical internal volume of the tip protector the D shaped clip forms a chamber for sound amplification between the flattened outer surface of the clip and the arcuate inner wall of the tip protector. This void space has been found to increase the perception of the click of the tab as it moves to its locked position. Additionally, by forming the tab out of a straightened section of the clip a substantially straight tab is formed. This tab has a substantially straight profile which therefore rides along the needle on a very thin contact area. It can easily be seen that by forming the clip out of a cylindrical piece of material wherein the tab is formed of a partially cylindrical surface the tab conforms slightly to the cannula and therefore increases the contact area and force necessary to slide the tip protector from its retracted position to its extended position. The embodiment as shown in FIG. 5B also has a slanted, eg. 30° angle, at its lead end. This feature along with the "D" shaped cylinder allow the anti-stick clip to be fed properly and presented to the tip protector interior at a preferred direction and rotation.

The sleeve material may be of any moisture impermeable or hydrophobic material. For example, polyester sheaths sold by E. I. dupont de Nemours company under the trademark DACRON formed into tubular portions have been found to work appropriately. Alternatively, a braided, knitted or woven fabric of polyester having a hydrophobic coating thereon may be used. The sheaths are moisture impermeable and therefore protect the user from fluids which may be found on the needle within the sheath material. The material of the sheath has sufficient tensile strength to provide the backward force to the tip protector necessary to prevent removing the tip protector far enough beyond the distal end 14 of the needle such that the needle may pass through the sleeve material. That is, the sleeve material provides the anchoring force which limits the travel of the tip protector beyond the end of the needle. If the sleeve material is too elastic the tip protector could be withdrawn passed the needle tip to a point where the needle tip was exposed to the sleeve material and provide the risk of puncturing the sleeve material with the needle tip. Therefore, a substantially inelastic material is desired such that the tip protector may be moved to its extended and locked position but not to any significant degree beyond that. The length of the tip protector base 13 is selected to substantially provide for any elasticity which may be present in the sleeve material and thereby reduce the risk of puncture of the sleeve material.

As mentioned above portion 17 may be formed with a gasket therein. In this device the term gasket may be used to describe any means which closes the access of bodily fluid to the internal portions and workings of the tip protector. For these purposes it may be an actual latex gasket or a mechanical valve like member which folds down over an opening in order to prevent the flow of fluid beyond the opening.

Examples of the gasket or valve like material are shown in FIG. 6. For example as shown in FIG. 6A the valve may take the shape of a living hinge similar to the clip 15. When the needle is withdrawn within the needle tip protector 11 the valve flap 23 folds from a position clearing the opening 24 to a position occluding the opening 24. This flap 23 may be made of suitable materials such as polyimide or polypropylene. It may be mounted within the tip protector by ultrasonic welding or other suitable techniques.

Figures 1, 6A:
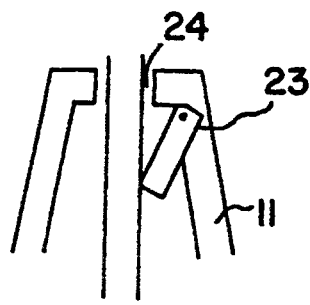
FIGS. 6A, 6B and 6C show various designs of a gasket means used in the present invention.
Figures 2, 6A:
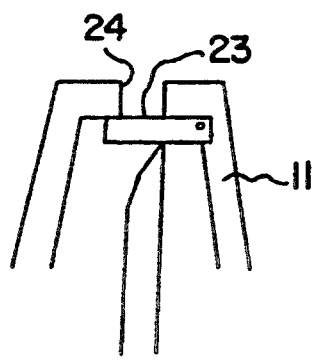
Figures 1, 6B:
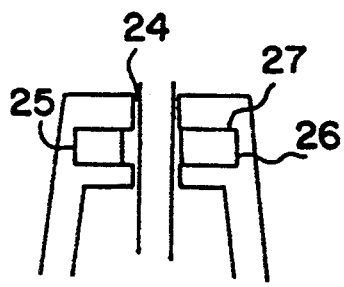
Figures 2, 6B:
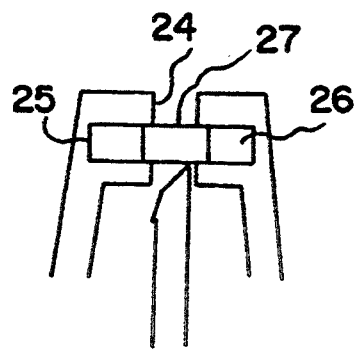

An alternative embodiment of the valve like means is shown in FIG. 6B wherein a magnet 25 is placed in a seat 26. A slidable metal piece 27 is provided on the opposite side of the opening. Once the needle or cannula is withdrawn through the opening the blockage provided by the needle is eliminated and the slidable metal piece 27 slides across the opening under the attraction of magnet 25. Thus the opening 24 is occluded preventing further blood flow back into the tip protector piece. It may be convenient in this type of structure to have the slidable metal piece act both as the anti-stick clip and a closing flap. That is, the metal piece in appropriate situations could be used as the clip to lock the protector over the tip of the cannula.

Figures 1, 6C:
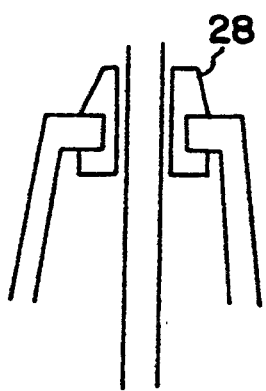
Figures 2, 6C:
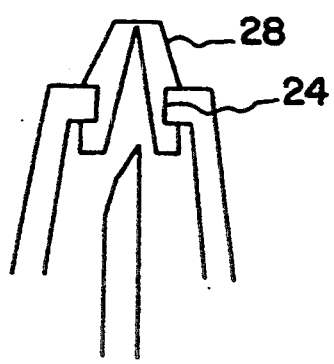

A further embodiment of the gasket like or valve like means is shown in FIG. 6C wherein a latex duck billed formation 28 is fitted into opening 24. The duck-bill formation has a naturally closed position, however, the receipt of the needle within the opening of the duck-bill portion maintains the portion open. When the needle is withdrawn the memory of the latex causes the duck-bill to close as shown in FIG. 5C thus preventing any further back flow of fluid into the tip protector.

We claim:
1. A catheter introducer assembly comprising:
A) a needle having a tip at a distal end thereof;
B) a hub attached at a proximal end of said needle;
C) a tip protector slidable along said needle said tip protector comprising:
1) means attaching said tip protector directly to said hub to limit movement of said tip protector beyond said tip said means for attaching being sufficiently flexible to permit compact storage;
2) holding means including a movable obstruction for obstructing the needle to for preventing movement of said tip protector toward said hub once said tip protector has been moved to a position covering said tip.

2. The apparatus of claim 1 further comprising a latex gasket formed in the tip protector to reduce back flow of fluid along the outer surface of the needle.

3. The apparatus according to claim 1 further comprising a valve within the tip protector to reduce the back flow of fluid from the catheter into the tip protector.

4. The apparatus according to claim 3 wherein said valve comprises a flap means which is moveable between a first position adjacent to an outer surface of said needle when said needle is within said tip protector but not withdrawn to a protected position and second position wherein said flap occludes a communication between said catheter hub and the inner space of said tip protector.

5. The apparatus of claim 4 wherein said flap rotates from said first position to said second position.

6. The apparatus according to claim 5 wherein said flap is a living hinge having sufficient resilient memory to move said flap from said first position to said second position.

7. The apparatus according to claim 4 wherein said flap is made of metal and slides in a direction transverse to said needle from said first position to said second position.

8. The apparatus according to claim 7 wherein a magnet is provided in the tip protector on a side of said needle opposite said flap in order to bias said flap toward said magnet to the position occluding communication.

9. The apparatus according to claim 7 wherein a spring is provided to bias said metal flap toward said second position.

10. The apparatus according to claim 1 wherein there is detent means formed on a first of said catheter hub and needle protector and a bump means is formed on the other to resist separation of said catheter hub and said tip protector.

11. In a catheter introducer product of the type having a tubular catheter having a hub at a proximal end thereof and an introducer needle received within the tubular catheter for introduction of the catheter into a patient; said introducer needle being in fluid communication with a needle hub comprising a flash chamber and further including anti-stick protection means which is slidable from a first position proximal said needle hub to a second position covering said needle tip; the improvement wherein said tip protector includes a substantially cylindrical clip having a flap formed in one surface thereof, said flap being plastically deformed inward into the inner space of said cylindrical clip.

12. The improvement according to claim 11 wherein said flap has a proximal end which is continuous with the remainder of said substantially cylindrical portion and a distal end having a substantially straight edge.

13. The improvement according to claim 11 wherein said clip has a flap having a proximal end which is substantially continuous with the remainder of said clip and a distal end cantilevered therefrom, said distal end having a curved shape.

14. The improvement according to claim 11 wherein said substantially cylindrical clip has a flat outer surface wherein said flap is formed and said flap is substantially planar.

15. The improvement according to claim 14 wherein said flap is substantially planar.

16. The improvement according to claim 15 wherein said substantially planar flap terminates in a curved edge.

17. The improvement according to claim 11 wherein said substantially cylindrical clip has a slanted lead end to facilitate presentation to the tip protector with a preferred orientation.

18. The improvement according to claim 11 wherein said tip protector is attached to said needle hub via a sleeve of material.

19. The improvement according to claim 18 wherein said sleeve of material is made of polyester.

20. The improvement according to claim 19 wherein said sleeve of material is selected from the group of materials, woven, nonwovens, braided and knitted fabrics.

21. The sleeve according to claim 20 further comprising a hydrophobic coating on said material to prevent the break through of fluid from the inner surface to the outer surface of said material.

22. A catheter introducer assembly having a needle, a needle tip at a distal end of said needle, a hub at a proximal end of said needle and a tubular catheter received over said needle, a protective element comprising;
 a) a tip cover slidable along said needle and defining a passage for receiving said needle;
 b) a flexible tubular restraint which receives said needle therein and extends between said tip cover at a distal end and a point adjacent said hub at a proximal end to restrain movement of said tip cover beyond and/off said needle tip; and
 c) a movable lock within said tip cover that moves from a first position adjacent said needle to a second position between said needle tip and said passage.

* * * * *